US010465209B2

(12) United States Patent
Noerholm et al.

(10) Patent No.: US 10,465,209 B2
(45) Date of Patent: *Nov. 5, 2019

(54) NON-PRESSURISED PRE-TREATMENT, ENZYMATIC HYDROLYSIS AND FERMENTATION OF WASTE FRACTIONS

(75) Inventors: Nanna Dreyer Noerholm, Fredericia (DK); Jan Larsen, Tommerup (DK); Frank Krogh Iversen, Odense (DK)

(73) Assignee: Renescience A/S, Fredericia (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/405,262

(22) Filed: Feb. 25, 2012

(65) Prior Publication Data

US 2012/0171732 A1 Jul. 5, 2012

Related U.S. Application Data

(62) Division of application No. 12/088,431, filed as application No. PCT/IB2006/002707 on Sep. 29, 2006, now Pat. No. 9,914,944.

(30) Foreign Application Priority Data

Sep. 30, 2005 (DK) .................................. 2005 01371

(51) Int. Cl.
*C12P 7/10* (2006.01)
*C12P 19/00* (2006.01)
(Continued)

(52) U.S. Cl.
CPC .................. *C12P 7/10* (2013.01); *B09B 3/00* (2013.01); *B09B 3/0091* (2013.01); *C12M 27/02* (2013.01);
(Continued)

(58) Field of Classification Search
CPC ......... Y02E 50/16; Y02E 50/10; Y02E 50/30; Y02E 50/32; C12P 19/14; C12P 7/10; C12N 9/2437
See application file for complete search history.

(56) References Cited

U.S. PATENT DOCUMENTS 2,954,285 A 9/1960 Carlssom et al.
4,093,516 A 6/1978 Lang
(Continued)

FOREIGN PATENT DOCUMENTS

CZ 9602835 A3 4/1998
DE 2746872 A * 4/1978
(Continued)

OTHER PUBLICATIONS

Angelidaki et al.: Thermophilic anaerobic digestion of source-sorted organic fraction of household municipal solid waste: Start-up procedure for continuously stirred tank reactor, Water research 40 (2006) 2621-2628.

(Continued)

*Primary Examiner* — Allison M Fox
*Assistant Examiner* — Qing Xu
(74) *Attorney, Agent, or Firm* — Womble Bond Dickinson (US) LLP

(57) ABSTRACT

The present invention relates to a process for production of fermentation products, including bioethanol by non-pressurized pre-treatment, enzymatic hydrolysis and fermentation of waste fractions containing mono- and/or polysaccharides, having a relatively high dry matter content. The process in its entirety, i.e. from non-pressurized pre-treatment over enzymatic hydrolysis and fermentation to sorting of fermentable and non-fermentable solids can be processed at a relatively high dry matter content in a single vessel or similar device using free fall mixing for the mechanical processing of the waste fraction.

20 Claims, 2 Drawing Sheets

Figure 1:
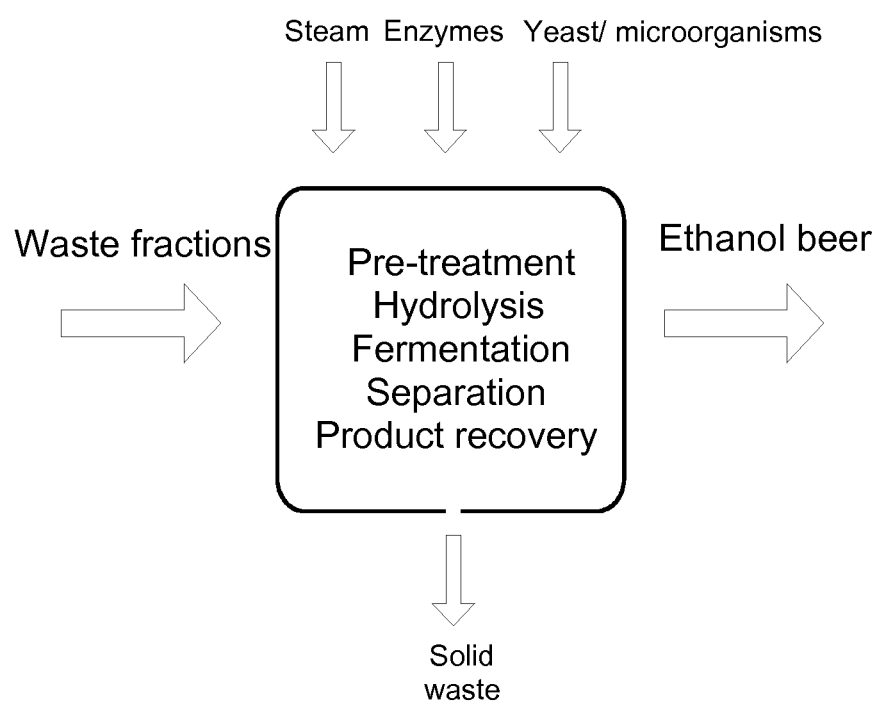

(51) Int. Cl.
 *B09B 3/00*    (2006.01)
 *C12M 1/06*    (2006.01)
 *C12M 1/08*    (2006.01)
 *C12M 1/00*    (2006.01)
 *C12P 7/06*    (2006.01)
 *C12N 9/42*    (2006.01)
 *C12N 9/48*    (2006.01)
 *C12N 9/26*    (2006.01)
 *C12N 9/20*    (2006.01)
 *C12N 9/24*    (2006.01)

(52) U.S. Cl.
 CPC ............ *C12M 27/06* (2013.01); *C12M 27/24* (2013.01); *C12M 45/04* (2013.01); *C12M 45/06* (2013.01); *C12M 45/20* (2013.01); *C12P 7/06* (2013.01); *C12P 19/00* (2013.01); *C12N 9/20* (2013.01); *C12N 9/2411* (2013.01); *C12N 9/2437* (2013.01); *C12N 9/2477* (2013.01); *C12N 9/48* (2013.01); *Y02E 50/16* (2013.01); *Y02E 50/17* (2013.01); *Y02E 50/343* (2013.01)

(56) References Cited

U.S. PATENT DOCUMENTS

| | | | |
|---|---|---|---|
| 4,094,740 | A | 6/1978 | Lang |
| 4,321,328 | A | 3/1982 | Hoge |
| 4,342,830 | A | 8/1982 | Holloway |
| 4,409,329 | A | 10/1983 | Silver |
| 4,540,495 | A | 9/1985 | Holloway |
| 5,009,370 | A | 4/1991 | Mackenzie |
| 5,190,226 | A | 3/1993 | Halloway |
| 5,407,809 | A | 4/1995 | Finn |
| 5,427,650 | A | 6/1995 | Halloway |
| 5,638,502 | A | 6/1997 | Scott et al. |
| 5,779,164 | A | 7/1998 | Chieffalo et al. |
| 5,865,898 | A * | 2/1999 | Holtzapple et al. ............ 127/37 |
| 6,000,639 | A | 12/1999 | Ganguli |
| 6,342,378 | B1 * | 1/2002 | Zhang et al. ................. 435/168 |
| 2004/0041301 | A1 | 3/2004 | Bouldin et al. |
| 2004/0057867 | A1 * | 3/2004 | Pijls ...................... A23C 3/0375 422/26 |
| 2005/0026262 | A1 | 2/2005 | Yoshitani et al. |
| 2005/0164355 | A1 * | 7/2005 | Vlasenko et al. ............ 435/101 |
| 2005/0166812 | A1 | 8/2005 | Noll et al. |
| 2007/0031919 | A1 | 2/2007 | Dunson, Jr. et al. |
| 2011/0008865 | A1 | 1/2011 | Lee |
| 2013/0029394 | A1 | 1/2013 | Toll et al. |

FOREIGN PATENT DOCUMENTS

| | | | |
|---|---|---|---|
| EP | 0120573 A1 | | 10/1984 |
| EP | 0921858 A1 | | 6/1999 |
| JP | 55155782 A | * | 12/1980 |
| JP | 2002-113444 A | | 4/2002 |
| JP | 2002-159954 A | * | 6/2002 |
| JP | 2002-159954 A1 | | 6/2002 |
| JP | 2002-186938 A1 | | 7/2002 |
| JP | 2002-355022 A1 | | 12/2002 |
| WO | WO82/01483 A1 | | 5/1982 |
| WO | WO02051561 A1 | | 7/2002 |
| WO | WO2006/056838 A1 | | 6/2006 |
| WO | 2008081028 A1 | | 7/2008 |
| WO | 2009108761 A1 | | 9/2009 |
| WO | 2009150455 A1 | | 12/2009 |
| WO | 2012006089 A1 | | 1/2012 |

OTHER PUBLICATIONS

Hartmann et al. A novel process configuration for anaerobic digestion of source-sorted household waste using hyper-thermophilic post-treatment, Wiley InterScience, Apr. 19, 2005.
Jokela et al: Hydrolysis rates, methane production and nitrogen solubilisation of grey waste components during anaerobic degradation, Bioresource Technology 96(2005) 501-508.
Pavan et al. Two-phase anaerobic digestion of source sorted OFMSW (organic fraction of municipal solid waste): performance and kinetic study, Water Science and Technology vol. 41 No. 3 pp. 111-118, 2000.
Lissens et al. Wet oxidation treatment of organic household waste enriched with wheat straw for simultaneous saccharification and fermentaion into ethanol, Environmental technology, May 11, 2000.
Rivers et al. Factors affecting the enzymatic hydrolysis of municipal-solid-waste components, Biotechnology and bioengineering, vol. 31 pp. 278-281, 1988.
Silva et al. Cellulase Activity of Trichoderma reesei (RUT-C30) on municiopal solid waste, Applied chemistry and biotechnology, vol. 51/52 1995.
Furusaki et al: Rotary Reactor Producing ethanol with immobilized yeast cells, Journal of the faculty of engineering, tokyo, JP. vol. 38, No. 1, Jan. 1985, pp. 1-7.
Giovannozzi_Sermanni et al: Solid-state bioreactors for the sustainability, Universita degli studi della Tuscia, Agricultural Biochemsitry Group.
Evans et al: Biofertiliser Plant Design—Food waste to biofertiliser and Biogas Mar. 27, 2007.
International Search Report and Written of the International Searching Authority for the International Applicatoin No. PCT/IB2006/002707, dated Jan. 31, 2007, European Patent Office, Berlin, Germany.
Office action dated Feb. 12, 2013 for parent U.S. Appl. No. 12/088,431.
Zuilichem et al, Journal of Food Engineering, 12 (1): 13-28, 1990.
Office action dated Jan. 18, 2013 issued for corresponding Canadian application No. 2,624,187.
Office action dated Apr. 12, 2013 issued for corresponding Australian application No. 2011250784.
Office action dated Jul. 25, 2013 issued for corresponding Indian Patent Application No. 3323/DELNP/2008.
Zhang et al, Municipal solid waste management in China; status, problems and challenges; Journal of Environmental Management 91 (2010) 1623-1633.
Examination Report of the New Zealand International Property Office for New Zealand Patent Application No. 567670, dated Dec. 13, 2010.
Office Action for related CA application No. 2,624,187.
International Searching Authority, Written Opinion for International Application No. PCT/IB2006/002707, dated Feb. 6, 2007, 5 pages, European Patent Office, Germany.
International Preliminary Examining Authority, International Preliminary Report on Patentability for International Application No. PCT/IB2006/002707, dated Dec. 4, 2007, 5 pages, European Patent Office, Germany.
Karak et al, Municipal Solid Waste Generation, Composition and Management; The World Scenario. Critical reviews in environmental science and technology, 42:1509-1630, 2012.
Riber et al. Chemical composition of material fractions in Danish household waste, wastemanagement 29 (2009) 1251-1257.

* cited by examiner

1. Outer stationary drum
2. Inner rotating drum, with some kind of perforation
3. Steam, enzymes, yeast and pH-adjustment addition points
4. Connection for product recovery
5. Product condenser
6. Temperature and pH-measuring

NON-PRESSURISED PRE-TREATMENT, ENZYMATIC HYDROLYSIS AND FERMENTATION OF WASTE FRACTIONS

This application is a divisional of co-pending U.S. application Ser. No. 12/088,431, which is the national stage entry of PCT/IB2006/002707, international filing date 29 Sep. 2006, which claims priority to PA 2005 01371 filed on 30 Sep. 2005.

FIELD OF THE INVENTION

The present invention relates to a process for production of bioethanol or other useful fermentation products by non-pressurised pre-treatment, enzymatic hydrolysis and fermentation of waste fractions containing mono- and/or polysaccharides, having a high dry matter content and optionally containing large particles. The whole process from non-pressurised pre-treatment over enzymatic hydroly and fermentation to sorting of fermentable and non-fermentable solids can be processed at high dry matter content in a single vessel without any transport of the mash. The mixing performed in this single vessel is based on a free fall mixing principle.

BACKGROUND OF THE INVENTION

Households, industrial and agricultural processes, municipality operations and food and feed processing generate waste fractions and by-products containing polymeric and/or monomeric sugars, e.g. in the form of glucose, starch, cellulose and hemicellulose. Today the majority of waste fractions generated in the households and industry are either deposited or incinerated. Deposition of waste fractions is connected with various environmental, health and logistic problems and is therefore becoming increasingly restricted in many countries, e.g. EU countries. The major alternative treatment is incineration of the waste. In countries with widely distributed district heating systems, e.g. Denmark, waste-to-energy plants converting the combustible waste to e.g. electricity and district heating, provide a quite good utilisation of the energy content of the waste. However, for the majority of countries without district heating systems pure power generation of the waste is provided with a very low efficiency.

Furthermore, incineration of waste does cause a lot of new environmental problems, mainly $NO_x$-, $SO_2$- and dioxin-emissions. Significant investment in flue gas cleaning systems can reduce, but not eliminate such problems. Furthermore approximately 20% of the waste are non-combustible and are deposited as slag and fly ash.

Nowadays parts of the slag are utilised as foundation materials in construction works, but future restrictions within such areas must be expected, mainly due to the fact that high content of heavy metal in the slag, could impede such an utilisation.

Thus, the vast amount of waste generated by modern society is becoming a problem with no obvious solutions. The local communities, industries as well as the society in general have considerable interest in developing processes for converting waste fractions in an environmentally friendly manner into materials of a higher value. Thus, by way of example various waste fractions could potentially be converted into bioethanol or other biochemicals by use of microorganisms and/or hydrolytic enzymes.

In general the key process steps in the production of bioethanol or other useful fermentation products from poly-, di- and monosaccharide containing waste fractions can be divided into five main steps, each step processed in one or more separate vessels:

Sorting and grinding of waste fractions
Pre-treatment
Hydrolysis
Fermentation
Product, e.g. ethanol, recovery The present invention surprisingly enables the steps of pre-treatment and hydrolysis to be performed in one and the same vessel in either a batch, semi-batch or continuous process and processes of the present invention do not as such rely on any previous sorting and grinding of the waste fractions. Furthermore, the fermentation, sorting and product, e.g. ethanol, recovery can also be performed in same vessel.

Sorting and Grinding of Waste Fractions

In process descriptions involving fermentation of non-homogeneous waste fractions, the first step is normally a very complicated process of sorting and grinding systems for the waste. The purpose is to gain an organic slurry capable of being processed in stirred tanks. The rest fractions should be recyclable to the widest extent. An example of such system is described in U.S. Pat. No. 4,094,740 A.

Pre-Treatment

Pre-treatment in general is required if subsequent hydrolysis (e.g. enzymatic hydrolysis) of the polysaccharides requires the break down of an otherwise protecting structure (e.g. lignin) of plant materials. Several pre-treatment techniques are known within e.g. the field of bioethanol production. Pre-treatment-processes may be based on e.g. acidic hydrolysis, steam explosion, oxidation, extraction with alkali or ethanol etc. A common feature of the pre-treatment techniques is that combined with the action of possible added reactants they take advantage of the softening and loosening of plant materials that occurs at temperatures above 100° C., i.e. a process requiring the application of pressure.

Hydrolysis

Following the pre-treatment and optionally the mechanical pre-treatment, the next step in the utilisation of mono- and/or polysaccharide-containing waste fractions for production of bioethanol or other biochemicals is hydrolysis of the liberated starch, cellulose and hemicellulose into fermentable sugars. If done enzymatically it requires a large number of different enzymes with different modes of action. The enzymes can be added externally or microorganisms growing on the biomass may provide them.

Cellulose is hydrolysed into glucose by the carbohydrolotic cellulases. The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanases (EG) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves off glucose units from cellooligosaccharides.

The different sugars in hemicellulose are liberated by the hemicellulases. The hemicellulytic system is more complex than the cellulolytic system due to the heterologous nature of hemicellulose. The system involves among others endo-1, 4-β-D-xylanases (EC 3.2.1.8), which hydrolyse internal bonds in the xylan chain; 1,4-β-D-xylosidases (EC 3.2.1.37), which attack xylooligosaccharides from the non-reducing end and liberate xylose; endo-1,4-β-D-mannanases (EC 3.2.1.78), which cleave internal bonds; 1,4-β-D-mannosidases (EC 3.2.1.25), which cleave mannooligosaccharides to mannose. The side groups are removed by a number of enzymes; α-D-galactosidases (EC 3.2.1.22), α-L-arabinofuranosidases (EC 3.2.1.55), α-D-glucuronidases (EC 3.2.1.139), cinnamoyl esterases (EC 3.1.1), acetyl xylan esterases (EC 3.1.1.6) and feruloyl esterases (EC 3.1.1.73).

The most important enzymes for use in hydrolysis of a polysaccharide such as starch are alpha-amylases (1,4-α-D-glucan glucanohydrolases, (EC 3.2.1.1). These are endo-acting hydrolases which cleave 1,4-α-D-glucosidic bonds and can bypass but cannot hydrolyse 1,6-alpha-D-glucosidic branchpoints. However, also exo-acting glycoamylases such as beta-amylase (EC 3.2.1.2) and pullulanase (EC 3.2.1.41) can be used for starch hydrolysis. The result of starch hydrolysis is primarily glucose, maltose, maltotriose, α-dextrin and varying amounts of oligosaccharides. When a starch-based hydrolysate is used for fermentation addition of proteolytic enzymes can be advantageous. Such enzymes may prevent flocculation of the microorganism and may generate amino acids available to the microorganism.

In combination with pre-treatment and enzymatic hydrolysis of lignocellulosic biomass, it has been found that the use of oxidative enzymes can have a positive effect on the overall hydrolysis as well as the viability of the microorganisms employed for e.g. subsequent fermentation. The reason for this effect is the oxidative crosslinking of lignins and other phenolic inhibitors as caused by the oxidative enzymes. Typically laccase (EC 1.10.3.2) or peroxidase (EC 1.11.1.7) are employed either externally or by incorporation of a laccase gene in the applied microorganism.

Fermentation

The fermentation process used in relation to the production of bioethanol or other useful fermentation products from waste fractions containing mono- and/or polysaccharides is basically a biochemical reaction that breaks down complex organic molecules such as mono- and or polysaccharides, into simpler constituents such as ethanol, carbon dioxide, and water, through the action of yeast (standard, cultivated or manipulated) and/or bacteria or any other microorganism capable of producing ethanol or other specific chemicals from the present hexoses and pentoses.

Product, e.g. Ethanol, Recovery

Recovery of the product, e.g. ethanol, from the fermentation beer is a standard process normally divided into three main processes: Beer stripping, where the solids are separated from the ethanol/water solution, rectification, where the ethanol is recovered from the watery solution and dehydration, where the last water is removed from the ethanol.

The recovery processes will not be described further, as the processes are very similar to standard distillation systems used e.g. in the starch and sugar based ethanol production industry.

Processes Showing Similarities to the Present Invention

Viewed separately pre-treatment and several of the subsequent process steps leading to the production of bioethanol from organic waste fractions have previously been described.

U.S. Pat. No. 4,342,830A describes a process for thermal pre-treatment of organic matter such as commercial, industrial, agricultural, household and restaurant waste in drum type mixer, with an inner perforated rotated drum and an outer stationary drum. The vessel is under pressure and steam is added to soften the organic matter of the waste. By momentary depressurisation of the outer drum, the softened organic matter is forced through the perforations of the inner drum, and a sorting of organic and inorganic matters is thereby performed. Hence, the waste is intensively grinded before further hydrolysis. The organic matter can subsequently be used for several purposes including ethanol production, however, neither these processes nor the hydrolysis is described as taking place in the same vessel as the pre-treatment.

U.S. Pat. No. 4,093,516A describes mechanical pre-treatment, thermal pre-treatment, chemical hydrolysis and saccharification, fermentation and recovery of ethanol, however, the method is based on waste fractions with a low dry matter content such as liquefied municipal waste or sewage.

CZ9602835A3 describes a process for production of ethanol based on lignocellulosic and starch containing materials. The materials are hydrolysed in a thermal pressure vessel of the drum type. Enzymatic hydrolysis of the remaining lignocellulose is performed in a different vessel and the resulting mash is transferred to still another fermentation vessel, hence, use of a single vessel for pre-treatment and hydrolysis is not suggested in this document.

U.S. Pat. No. 4,094,740A describes a process comprising a 15-step waste sorting system based on the wet-fractionation system for the production of ethanol from municipal solid waste. The organic waste is subsequently ground and hydrolysed by pressurised acid hydrolysis for e.g. subsequent ethanol production.

U.S. Pat. No. 5,637,502 describes a process for utilising municipal solid waste in ethanol production. The process operates with pulped waste with a dry matter content below 20%. The waste is heated under pressure in a stirred tank. The hydrolysis is performed with enzymes and the glucose produced is continuously recovered through a five-step sorting unit.

Differences Between Present Invention and Known Technologies

Thus, there is a need for a simplified process which can handle waste fractions with a high dry matter content and which also allows efficient treatment of only partly-organic waste fractions containing large particles of also non-organic origin. The present invention provides a process capable of handling un-sorted waste fractions directly and thereby avoids the use of large, costly and environmentally problematic sorting and grinding systems. For municipal solid waste, sorting at the source, or alternatively some kind of central sorting of organic and inorganic fractions is believed to enhance performance of processes according to the present invention. For other fractions a rough shredding of the waste to open up bags and reduce volume is believed to enhance performance of processes according to the present invention.

The pre-treatment in a process according to the present invention is performed at atmospheric pressure which reduces the energy cost, the equipment cost and the mechanical difficulties significantly. Further more no chemical addition is needed in the pre-treatment. Therefore the present invention is directed at waste fractions where the polysaccharides mainly are sugars, starch or already pre-treated cellulose as paper, cardboard or similar. Hereby the costs for enzymes also are kept low, as amylases in general are cheaper than cellulases. The aim of this process is to do a low-priced extraction of monosaccharides. Unconverted lignocellulosics can possibly be sorted out after the fermentation and used for instance in a process with high pressure pre-treatment.

The hydrolysis is in the present invention performed enzymatically without previous detoxification of the mash. Furthermore the hydrolysis is carried out on a mash with dry matter content above 20% w/w.

The fermentation in this invention is also performed without any prior detoxification. Chemical addition is only needed for pH-adjustment. Optionally the liquefied waste fraction could be lead to a standard fermenting vessel for further saccharification and fermentation.

The next process step of the production of bioethanol or other useful fermentation products optionally includes the sorting of the fermented or fermentable waste fractions from the non-fermentable solids. This step can be performed in the same vessels used for pre-treatment, hydrolysis and fermentation. By utilising the fact, that the hydrolysis liquefies the fermentable parts of the waste while the non-fermentable solids remain in the solid phase, a sorting can e.g. be performed by a sieve system incorporated in or external to the vessel.

Furthermore it is possible to perform the product, e.g. ethanol, recovery in one and same vessel. This can either be as a total recovery of e.g. ethanol from the fermented mash accomplished by heating and/or vacuum, or it can be a recovery of e.g. ethanol from the none-fermented solids remaining after the sorting.

Within the technical field of e.g. bioethanol production it has, so far, not been possible to perform pre-treatment and hydrolysis in one single vessel utilising the principle of free fall mixing, and even less to perform the total process from pre-treatment to product recovery in one vessel.

The principle of gravity mixing can be applied for all kinds of waste fractions even with high viscosity or presence of large entangling particles with low energy inputs and allows easy scale up. Another object of the present invention is to reduce energy input in pre-treatment by using non-pressurised pre-treatment. It has surprisingly been found, that treatment of non-shredded, partly-organic waste fractions with a dry matter content above 20% according to the present invention, result in enzymatic hydrolysis of more than 50% of the cellulose, hemicellulose and starch originally present in the waste into cellobiose, glucose and xylose. Furthermore, an ethanol content above 4 vol. % is obtainable without adding other fermentable raw materials.

SUMMARY OF THE INVENTION

The present invention relates to a process for non-pressurised pre-treatment, liquefaction, saccharification, fermentation and sorting of mono- and/or polysaccharide containing waste fractions. The process is suitable for waste having a relatively high dry matter content, preferably above 20%, and including relatively large particles. Unlike conventional processes the process according to the present invention additionally allows for efficient treatment of partly organic waste fractions including large particles. The treatment of said material can be carried out without additional water supply, detoxification or mechanical shredding.

The pre-treatment can optionally be performed by steam admission without the application of pressure, i.e. the vessel is open to the atmosphere, and the pre-treatment time is relatively short, i.e. in the range of 0 to 120 minutes.

A further characteristic of the present invention is the fact that the pre-treatment and the hydrolysis will be performed in one single vessel. Furthermore the vessel could optionally be used in the carrying out of the fermentation and the separation of the fermentable broth from the non-fermentable solid fractions by a sieve concept (cf. FIGS. 1 and 2). Product, e.g. ethanol, recovery from either the total fermentation mash or the solid fraction could also be performed in said vessel. The concurrent mixing of the waste fractions is performed in a mixing device, which primarily relies on the principle of gravity in order to ensure the necessary mechanical action of the waste fraction. Preferred types of mixing devices are free fall mixers, such as drum mixers, tumble mixers or similar devices. Furthermore, the process is particularly suited for the bioethanol production of mono- and/or polysaccharide containing waste fractions with high content of starch, refined starch, cellulose, hemicellulose and monosaccharides.

The enzymatic hydrolysis is based on the combination of hydrolytic enzymes including carbohydrolytic enzymes, as well as oxidative enzymes. The fermentation is performed with yeast or any other kind of ethanologenic microbes, i.e. microorganisms capable of utilising pentoses and/or hexoses for the production of bioethanol or other biochemicals.

DESCRIPTION OF THE INVENTION

Mechanical Action on the Mono- and/or Polysaccharide Containing Biomass

Figure 2:
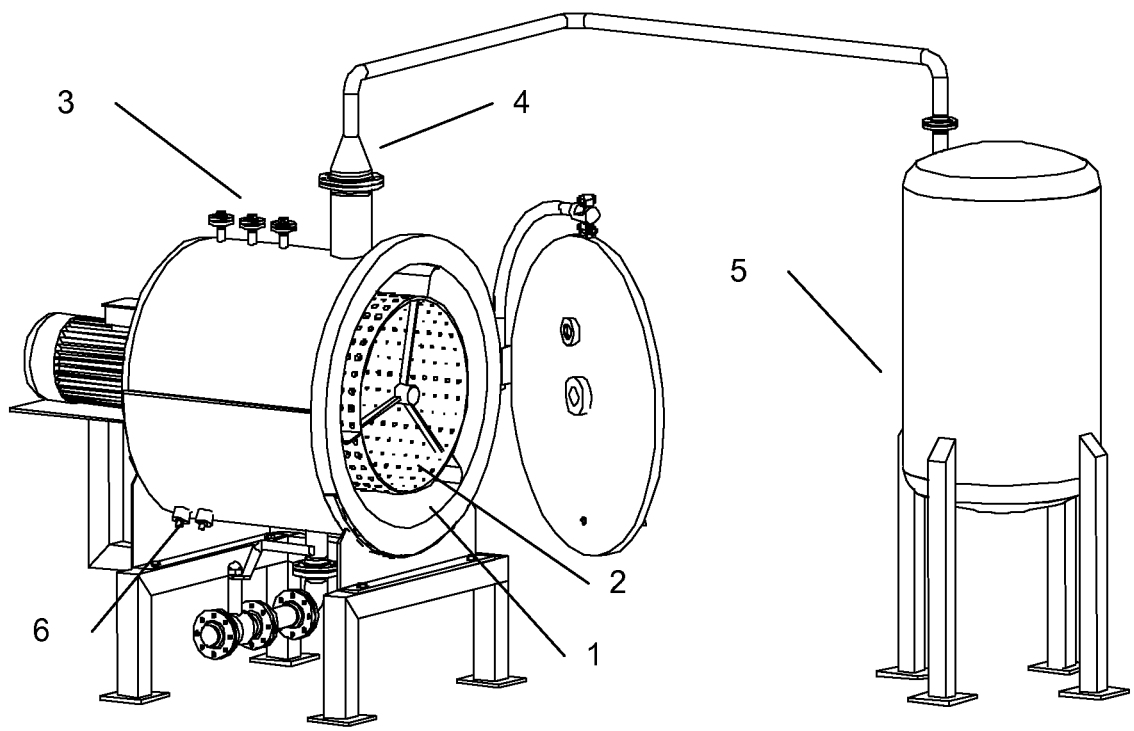

The present invention includes three process steps, i.e. non-pressurised pre-treatment, enzymatic hydrolysis and fermentation. In addition steps for sorting/recovery of waste fractions and fermentation product may be included. Pre-treatment and hydrolysis is carried out in one single vessel, while the fermentation, sorting and product recovery optionally can be carried out in one and the same vessel as the pre-treatment and hydrolysis. Within the technical field of bioethanol production it has not previously been shown how to integrate such process steps in one single vessel. Numerous prior art documents, such as U.S. Pat. No. 4,342,830A, CZ9602835A3 and U.S. Pat. No. 4,094,740A are describing starting materials and process steps similar to the ones claimed in the present invention. However none of them describe non-pressurised pre-treatment or the integration of pre-treatment and hydrolysis in a single vessel, reactor or similar device. The vessel according to the present invention is based on a free fall mixing principle, i.e. a drum mixer, a mixer with a rotary horizontal axis lifting the waste or similar mixing devices utilising a free fall principle (cf. FIG. 2, showing an example of such mixing device).

The mixing performed in all process-steps according to the present invention serves at least a four-fold purpose.

Firstly, it ensures close contact between the poly- and/or monosaccharide containing waste fractions and the steam, enzymes as well as the microorganisms used.

Secondly, the mechanical work performed on the material during the free fall mixing helps tearing larger particles apart and will therefore assist in increasing the surface area of the material which moreover will increase the accessibility of e.g. cellulose and hemicellulose to the enzymes used. To further increase the mechanical work on the material, steel balls or similar means that will collide with the material may optionally be added to the mixer.

Thirdly, the mixing of the material prevents local accumulation of high cellobiose concentration that—as is well known for a person skilled in the art—can inhibit e.g. cellulase enzymes, especially the cellobiohydrolases.

Fourthly, an important characteristic of the cellulase enzymes is the influence of cellulose binding domains (CBD) on the enzyme performance. CBD's are functional parts of cellulose degrading enzymes. The CBD enables adhesion of the water-soluble enzyme onto an insoluble substrate surface (cellulose). The close association between the enzyme and cellulose provided by the CBD enhances the catalytic rate and stability of the enzyme. To hydrolyse cellulose, the enzyme must change the position of the CBD on the cellulose chain. It is believed that mechanical action, i.e. free fall mixing, is important for the movement of the CBD and consequently for the enzymatic action of the enzymes along the cellulose chain.

In addition to the above it should be noted that enzymatic hydrolysis and fermentation has traditionally been conducted in stirred tank reactors equipped with impellers, e.g. Rushton turbine or Intermig impeller, mounted on a centrally placed impeller shaft similar to what is used in the grain fermentation industry. Using this equipment, solutions of high viscosity, very sticky or very dry material cannot be stirred efficiently but will result in zones with very poor or no mixing. Furthermore, stirrings of such mixtures require very large energy inputs, which is detrimental to the process economy. Operating with mono- and/or polysaccharide containing waste fractions this has previously restricted the upper limit of the dry matter content to approximately 20%. The free fall based mixing principle overcomes this problem and may be used for poly- and/or monosaccharide containing waste fractions with dry matter content above 20%.

Although processing of non-miscible plant materials such as e.g. mono- and/or polysaccharide containing biomass with relatively high dry matter content and large average fibre and particle size, is known from solid-state fermentation or bioreactors, where tumble type mixers are used for blending (e.g Giovanozzi et al. 2002), this mixing principle has not previously been implemented in a combined single vessel process, comprising non-pressurised pre-treatment, enzymatic hydrolysis and optionally fermentation and sorting of mono- and/or polysaccharide containing waste fractions.

Non-Pressurised Pre-Treatment

One example of the non-pressurised pre-treatment of the waste fraction as claimed in the present invention is a non-pressurised steam pre-treatment. This deviates significantly from previously described pre-treatments of similar biomasses, e.g. U.S. Pat. Nos. 4,342,830A, 4,093,516A, CZ9602835A3, U.S. Pat. Nos. 4,094,740A and 5,637,502 the processes of which are all being carried out under pressure. The non-pressurised pre-treatment according to the present invention could be conducted by injecting steam directly into the vessel and/or by heating the vessel indirectly. Optionally pH adjustment can be used in order to improve the impact of the pre-treatment. The pre-treatment of the waste fraction is applied simultaneously with the free fall based mixing.

The purpose of the pre-treatment according to the present invention is to minimize the amount of unwanted microorganisms through biocidal activities prior to the actual enzymatic treatment. Examples of such activities are radioactive radiation, UV-radiation and electroporation. By using thermal treatment as an option, softening of processed biomass such as various paper fractions, break down of the internal structure of biomass with high water content and low lignin content such as vegetables, and opening of starch structures occurs in addition to the biocidal effect. If a proper performance of the subsequent hydrolysis of the polysaccharides requires the decomposition of an otherwise protecting structure (e.g. lignin) of the original lignocellulosic material, a pressurised pre-treatment might be required. However, the purpose of the pre-treatment according to the present invention is not to break down protecting structures of non-processed biomass or the like, but rather to delimit microbial activity and to soften the processed waste fraction. The non-pressurised pre-treatment process is preferably based on steam admission, but can optionally be supplemented with acidic or alkali compounds.

The non-pressurised pre-treatment of the mono- and/or polysaccharide containing waste fractions according to the present invention preferably utilises steam to heat up the waste to approximately 100° C. This significantly deviates from previously described pre-treatments within the technical field, e.g. the process described in U.S. Pat. No. 4,342,830A, in which pressurised pre-treatment of the substrate is utilised. Utilisation of biomass/substratum with a high dry matter content, such as the waste fractions according to the present invention, in the production of bioethanol and the utilisation of free fall mixing throughout all steps of the process has not previously been described.

All fractions described, may optionally be subjected to some sort of mechanical pre-treatment such as sorting, shredding or pulping before being utilised in the actual processes according to the present invention. However, the mechanical pre-treatment as such does not constitute part of the invention. In the majority of previously described processes for the production of bioethanol, e.g. CZ9602835A3, U.S. Pat. Nos. 4,094,740A and 5,637,502 it has been an absolute necessity to shred, pulp or otherwise reduce the particle size of the used biomass/substratum in order to carry out the ethanol production properly. The process according to the present invention can handle and process mono- and/or polysaccharide containing waste fraction with dry matter contents above 20% and containing large particles, without additional water supply or mechanical shredding which is an obvious advantage in relation to e.g. the process economy.

Hydrolysis

Following the non-pressurised pre-treatment, the next step in the utilisation of mono- and/or polysaccharide containing waste fractions for production of bioethanol or other biochemicals is hydrolysis of the liberated starch, cellulose and hemicellulose into fermentable sugars. If done enzymatically this requires a large number of different enzymes with different modes of action. The enzymes can be added externally or microorganisms growing on the biomass, i.e. the waste fraction, may provide them.

Before adding enzymes or enzyme producing microorganisms the temperature and pH must be adjusted according to the optima for the enzymes in question. Cooling and heating of the mash could optionally be performed by circulating cold or hot water (e.g. district heating water) through a vessel jacket or by injecting steam or cold water directly into the vessel. Prior to the enzymatic hydrolysis it may be necessary to add additional water in order to reach an appropriate dry matter content, though still exceeding 20%, for the enzymes. The pH can be adjusted continuously by injecting diluted acid or alkaline solutions into the vessel. Furthermore the pH can be controlled by an on-line pH-metering unit.

The purpose of the enzymatic hydrolysis process is partly to kick start the liquefaction at optimal enzyme conditions, which often deviates from optimal fermentation conditions, and partly to liquefy fractions of the waste in order to reduce viscosity and thereby prepare the fraction for the subsequent saccharification and fermentation. The duration of the hydrolysis step could be from 0 to 24 hours depending on the composition and consistency of the waste fraction.

Enzymes capable of effecting a conversion of starch, cellulose and hemicellulose or parts thereof into glucose, xylose and cellobiose are added to the biomass either in native form or in form of microbial organisms giving rise to the accumulation of such enzymes. Special mixes of enzymes will be produced for each individual waste fraction depending on e.g. the composition of the fraction. Other additives may likewise be added in order to enhance the enzyme activity.

Fermentation

The fermentation process can be performed in the same vessel at which the non-pressurised pre-treatment as well as the enzymatic hydrolysis previously took place. Optionally the partly fermented mash could be transported to another fermentation vessel for end-fermentation.

The fermentation process is performed by adding yeast (standard, cultivated or manipulated), thermophilic bacteria or any other microorganism capable of producing bioethanol or other specific biochemicals from the hexoses and pentoses present in the partly hydrolysed mash. Addition of further enzymes to the mash concurrently with the addition of yeast is preferred under certain circumstances. Before the fermentation can start and during the fermentation process itself, the temperature and pH of the mash is optionally adjusted according to the pH and temperature optima of the microorganisms used. The fermentation may be anaerobic and yeast or other ethanologenic microorganisms may be added externally (e.g. from seed fermentors). Alternatively the microorganisms may be grown in the fermentation process itself by adding air, oxygen or any other oxygen-containing additive to the fermentation. For some waste fractions it may be necessary to add e.g. nitrogen sources, nutrients as well as vitamins in order to carry out the fermentation process properly.

Alternatively the fermentation process could include continuous ethanol recovery or recovery of other biochemicals from the vessel, depending on the operation temperature.

Sorting of Non-Fermentable Fractions

Sorting of the fermented or fermentable fractions from the non-fermentable solids could be carried out in the same vessel used for the non-pressurised pre-treatment, enzymatic hydrolysis and fermentation. As the hydrolysis liquefies or partly liquefies the fermentable parts of the waste fraction while most non-fermentable solids remains in the solid phase, a sorting can be performed by e.g. a sieve system incorporated in the vessel.

The incorporated sieve system could e.g. be a rotating drum with inner perforations carrying out the mixing and separating the non-converted solids from the liquefied solids. Alternatively it could be a sieve device in a stationary drum, which is kept clean by the rotating mixing devices. The purpose of the sorting step is to retain the main part of the final product, e.g. bioethanol, in the liquid phase while the main part of the non-convertible solids will remain in the solid fraction. The product left in the solid fraction of the vessel could be recovered by heating the fraction to above its boiling point and subsequently condensing the vapours before emptying the vessel.

DETAILED DESCRIPTION OF THE INVENTION

FIG. 1 shows a schematic diagram of the principle of the invention. In the example shown, waste is placed in a vessel wherein non-pressurised pre-treatment, hydrolysis, fermentation and separation are performed by the addition of steam, enzymes and yeast/microorganisms. The ethanol beer is optionally removed for further processing while the solid waste is discharged.

FIG. 2 shows an example of a gravity mixer suitable for the present invention. A perforated inner-drum separates the fermentable and non-fermentable waste fractions. The process according to the present invention can be performed using the following preferred technical parameters.

For all waste fractions, the particle size is no limitation for processing the waste. Only the dimension of the equipment could limit the maximum particle size of the waste. It is therefore possible to handle and utilise un-sorted un-shredded waste with e.g. particles of 1000 mm throughout the total process.

Composition of the Mono- and/or Polysaccharide Containing Waste Fraction

Mono and/or polysaccharide containing waste fractions according to the present invention include any materials containing polymeric and/or monomeric sugars e.g. in the form of starch as well as refined starch, cellulose, hemicellulose and/or di- and/or monosaccharides. Treatment of the below-characterised material can be performed without supplementary addition of water or mechanical shredding.

Relevant types of mono- and/or polysaccharide containing waste may include:

waste fractions derived from households such as e.g.:
Unsorted municipal solid waste (MSW)
MSW processed in some central sorting, shredding or pulping device such as e.g. Dewaster® or reCulture®
Solid waste sorted from households, including both organic fractions and paper rich fractions.
RDF (Refuse-Derived-Fuel) fractions.
Waste fractions derived from the industry such as e.g.:
General industry waste fractions containing paper or other organic fractions now being treated as household waste.
Waste fraction from paper industry, e.g. from recycling facilities
Waste fractions from food and feed industry
Waste fraction from the medicinal industry
Waste fractions derived from agriculture or farming related sectors such as e.g.:
Waste fractions from processes including sugar or starch rich products such as potatoes and beet.
Contaminated or in other ways spoiled agriculture products such as grain, potatoes and beet not exploitable for food or feed purposes.
Garden refuse
Manure, or manure derived products
Waste fractions derived from municipal, county or state related or regulated activities such as e.g.:
Sludge from waste water treatment plants
Fibre or sludge fractions from biogas processing
General waste fractions from the public sector containing paper or other organic fractions
The dry matter content of the mono- and/or polysaccharide containing waste fraction in the enzymatic hydrolysis and fermentation processes is above 20%, preferably 20-80%, more preferably 20-50%, even more preferably 20-45% and most preferably 20-40%

Free Fall Mixer Device

If a vessel based on the free fall mixing concept in the form of a drum mixer is utilised, the following technical data are preferred:

Rotational speed: 0-30 rpm, preferably 0-20 rpm, more preferably 0-15 rpm even more preferably 0-10 rpm and most preferably 0-5 rpm.
Rotation with periodically alternated rotating direction.
Rotation in pre-defined intervals.

As will be evident the optimal rotational speed will depend on the volume of the vessel, the preferred rotational speed may thus be relatively high when the process is carried out in a relatively small vessel, while it may be relatively low when the process is carried out in a relatively large vessel.

Non-Pressurised Pre-Treatment of Waste Fractions

If a thermal pre-treatment is chosen the following technical data is preferred:

Pre-treatment temperature: 60-110° C., preferably 65-105° C., more preferably 70-105° C., even more preferably 75-105° C. and most preferably 80-100° C.

Pre-treatment time: 0-120 min, preferably 5-100 min, more preferably 10-90 min, even more preferably 20-80 min and most preferably 30-60 min.

Pre-treatment steam admission: 0-2 kg/kg dry matter, preferably 0.01-1.5 kg/kg dry matter, more preferably 0.02-1.0 kg/kg dry matter, even more preferably 0.03-0.8 kg/kg dry matter and most preferably 0.05-0.5 kg/kg dry matter.

Enzymatic Hydrolysis of Waste Fractions

Enzymes for hydrolysis of various waste fractions:
  Cellulases
  Cellobiases
  Hemicellulases
  Alpha amylases
  Glyco amylases (AMG)
  Oxidative enzymes
  Optionally proteolytic enzymes and lipases Treatment time for enzymatic hydrolysis: 0-96 hours, preferably 0-72 hours, more preferably 0-48 hours, even more preferably 0-24 hours and most preferably 5-15 hours Temperature for enzymatic hydrolysis (adjusted with reference to the optimum temperatures of the applied enzymes): 20-105° C., preferably 20-100° C., more preferably 20-90° C., more preferably 20-80° C., even more preferably 25-70° C. and most preferably 30-70° C.

pH of waste mash (adjusted with reference to the optimum pH of the applied enzymes): 3-12, preferably 4-11, such as 5-10, more preferably 4-9, such as 6-9, even more preferably 4-8, such as 7-8 and most preferably 4-5.

Fermentation of Hydrolysed Waste Fraction

Microorganisms for fermentation of various waste fractions.
  Standard bakers yeast (dry, fresh or in any other form)
  Any kind of genetically or otherwise modified yeast
  Any kind of thermophilic bacteria
  Any kind of fungus capable of producing the desired product.

Treatment time for fermentation: 1-150 hours, preferably 10-90 hours, more preferably 20-80 hours, even more preferably 30-75 hours and most preferably 40-70 hours.

Temperature for fermentation (adjusted with reference to the optimum temperatures of the applied microorganisms): 20-105° C., preferably 20-100° C., more preferably 20-90° C., more preferably 20-80° C., even more preferably 25-70° C. and most preferably 30-70° C.

pH of waste mash. Adjusted with reference to the optimum pH of the applied micro organisms: 3-12, preferably 4-11, such as 5-10, more preferably 4-9, such as 6-9, even more preferably 4-8, such as 7-8 and most preferably 4-5

Example 1: Experiments with High Cellulase Loading Conducted in a Cement Mixer 1) Ethanol Production from Untreated Municipal Solid Waste 12.2 kg of unsorted and untreated municipal solid waste from Odense Kraftvarmeværk's waste pit, corresponding to an estimated amount of 8.5 kg dry matter, was loaded into a conventional rotary cement mixer, with a horizontal axis tilted about 10 degrees. The mixer consisted of two internal ribs along the long axis in order to ensure proper mixing of the material. A lid was mounted on the opening in order to keep the waste fraction inside the drum and to reduce evaporation from the mixer. The mixer drum rotated along the horizontal axis with a speed of 29 rpm.

A steam generator was connected to the rotating drum. Approximately 4.5 kg of saturated steam at 3 barg was added during a period of 35 minutes, of which 20 minutes was used to heat up the waste fraction and the remaining 15 minutes was retention time at 90-96° C.

The cement mixer was cooled down to 40° C. by removing the steam connection and a fan heater was mounted in order to keep a constant temperature in the range of 40-45° C. Two liters of water was added resulting in a dry matter content of the mash of 45%.

1275 ml of Celluclast® 1.5 FG L, 255 ml of Novozym® 188 and 8.5 ml of AMG were added to the waste mash. The Celluclast® 1.5 FG L and Novozym® 188 enzyme addition corresponded to approximately 15 FPU/g DM.

The cement mixer was heated to 40-45° C. by use of a fan heater. The mixing/hydrolysis of the material was performed over 9 hours and was interrupted every hour in order to measure the pH level and adjust it to 4-5. The pH of the mash was adjusted by adding citric acid granulates to the drum. The process resulted in a more or less muddy mash containing large non-converted particles, such as plastic containers, tins and pieces of glass. Samples were taken.

In order to determine the sugar content of the resulting samples, they were centrifuged for 15 min at 2500 rpm after which the supernatant was filtered through a 0.45 μm filter and analysed for sugars on HPLC. After 9 hours of enzymatic hydrolysis at an enzyme load of 15 FPU/g DM the supernatant contained 51 g/kg of glucose and 10 g/kg of xylose.

After 9 hours of hydrolysis at 40-45° C. the saccharification and fermentation processes were performed simultaneously by adding yeast to the cement mixer. The temperature was allowed to cool down below 35° C. after which 170 g of compressed yeast (Baker's yeast, De Danske Spritfabrikker) was added. The saccharification and fermentation processes were continued for 37 hours at 30-35° C. only interrupted once for pH adjustment after 16 hours.

The simultaneous saccharification and fermentation resulted in 32 g/kg of ethanol equivalent to 4.5 vol. % of ethanol.

The fermented mash was sieved and the solid fraction dried. The dry solid fraction made up 4.6 kg. The dry matter of the liquid fraction was not further analysed.

2) Ethanol Production from Source Sorted Organic Solid Household Waste 25.7 kg of source sorted municipal solid waste from deposal area Klintholm WS corresponding to an estimated amount of 10.3 kg dry matter was handled in the same way as described above. The steam admission resulted in a dry matter content of the mash at approximately 30%.

1545 ml of Celluclast® 1.5 FG L, 309 ml of Novozym® 188, 10 mL of Spirizyme® plus FG (glyco amylase) and 10 ml of Liquozyme® sc ds (alpha amylase) were added to the waste mash. The Celluclast® 1.5 FG L and Novozym® 188 enzyme addition corresponded to approximately 15 FPU/g DM.

The cement mixer was heated to 40-45° C. by use of a fan heater. The mixing/hydrolysis of the material was performed for 6 hours and was interrupted every hour in order to measure and adjust the pH to 4-5. The pH of the mash was adjusted by adding citric acid granulates to the drum. The process resulted in semi-liquid mud containing minor amounts of non-converted particles such as pieces of plastic, tins and glass.

The samples were centrifuged for 15 min at 2500 rpm. The supernatant was filtered through a 0.45 μm filter and analysed for sugars on HPLC. After 6 hours of hydrolysis and at an enzyme load of 15 FPU/g DM, the supernatant contained 53 g/kg of glucose and 12 g/kg of xylose.

After 6 hours of hydrolysis at 40-45° C. the saccharification and fermentation processes were performed simultaneously by the addition of yeast to the cement mixer. The temperature was allowed to cool down below 35° C. and 200 g of compressed yeast (Baker's yeast, De Danske Spritfabrikker) was added. The saccharification and fermentation processes were continued for 39 hours at 30-35° C. only interrupted once after 13 hours for pH adjustment.

The simultaneous saccharification and fermentation resulted in 37 g/kg of ethanol equivalent to 5.2 vol. % of ethanol.

After sieving of the fermented mash the wet solid fraction made up 6.0 kg. The dry matter of the liquid fraction was not further analysed.

Example 2: Experiment with High Cellulase Loading Conducted in Pilot Scale Reactor (FIG. 2)

Ethanol Production (Including Vacuum Stripping) from Source Sorted Organic Solid Household Waste and Paper 49.6 kg of source sorted municipal solid waste from deposal area Klintholm WS and 16.7 kg paper (newspapers and advertising circulars) corresponding to an estimated amount of approximately 33.3 kg dry matter was loaded into the pilot reactor. The pilot reactor is consisting of a stationary drum with a perforated inner drum as can be seen on FIG. 2, the perforated inner drum can rotate along the horizontal axis (in alternating directions with a speed of 0-18 rpm). The reactor is equipped with a cooling/heating jacket for temperature control, which is connected to an electrical heating element and to cooling water. The reactor can also be connected to a vacuum stripper for ethanol recovery.

Approximately 21 kg of saturated steam at 4 barg was added during a period of 60 minutes while mixing—30 min heating and 30 min pre-treatment at 90° C. To further lower the dry matter content of the waste mash 15 l of water was added, which resulted in a dry matter content of 30-32%.

After the pre-treatment the reactor and content was cooled to approximately 40° C. with cooling water in the cooling jacket of the reactor and addition of small amounts of pressurised air to the drum.

Prior to addition of enzymes the pH of the waste fraction was adjusted to approximately 5. After this 5 l of Celluclast® 1.5 FG, 1 l Novozym® 188, 33 ml Spirizyme® plus FG and 33 ml Liquozyme® sc ds was added. The amount of Celluclast® 1.5 FG and Novozym® 188 corresponds to an enzyme dose of approximately 15 FPU pr. g dry matter.

During enzymatic hydrolysis the pH of the waste mash was continuously adjusted by addition of solid citric acid to the drum. Hydrolysis changed the consistency of the waste mash from a solid to a semi liquid mud containing minor amounts of non-converted particles such as pieces of plastic, nutshells and small sticks.

After 6 hours of hydrolysis at 40-45° C. the waste mash was cooled to 36° C. with cooling water in the cooling jacket and small amounts of pressurised air in the drum. After cooling 666 g compressed Baker's yeast (De Dansk Spritfabrikker) was added to the drum. The simultaneous saccharification and fermentation (SSF) processes were continued for 39 hours at 30-35° C.

The hydrolysis and the subsequent SSF process, i.e. after 45 hours in total, resulted in 28.8 g/kg of ethanol equivalent to 4.0 vol. % of ethanol.

After SSF some the ethanol in the reactor was recovered by connecting a vacuum pump and a cooled condenser to the reactor.

Example 3: Experiment with Low Cellulase Loading Conducted in Pilot Scale Reactor (FIG. 2)

Ethanol Production from Unsorted Municipal Solid Waste and Paper 32.1 kg of MSW from two families in one week was added in closed waste bags and 8.1 kg additional paper (newspapers and advertising circulars) corresponding to an estimated amount of approximately 30 kg dry matter was loaded into the pilot reactor. To lower the dry matter content of the waste 12.5 l water was added. For detailed description see example 2.

After loading the waste was heated to 90° C. with the heating jacket and additional steam (4 barg) to the reactor chamber. When 90° C. (also checked manually by a hand-held thermometer inside the drum) was reached, the temperature was kept there for 30 minutes while mixing. Afterwards the mixture was cooled to approximately 50° C. with the cooling jacket while the pH was adjusted to approximately 5 by addition of solid citric acid.

At correct temperature and pH, enzymes were added in the form of: 1.15 l Celluclast® 1.5 FG, 0.25 l Novozym® 188, 30 g amylase (NS50033, from Novozymes), 15 g Resinase® A 2× and 15 g Alcalae® 2.5 L. The amount of Celluclast® 1.5 FG and Novozym® 188 corresponds to an enzyme dose of approximately 7 FPU pr. g dry matter.

During the enzymatic hydrolysis the pH of the waste mash was continuously adjusted by addition of solid citric acid to the drum.

Approximately 24 hours after addition of enzymes the now viscous waste was further chilled to 33° C. and the yeast was added. Soon after the addition of yeast carbon dioxide formation could be observed as bubbles in the yeast lock. During SSF, pH of the mash was adjusted by addition of solid sodium carbonate. The process continued for one week.

After 24 hours of pre-hydrolysis followed by seven days of SSF the result was 22.8 g/kg of ethanol equivalent to 3.2 vol. % of ethanol.

Example 4: Yields (Waste to Ethanol) for Different Types of Waste

Several experiments have been conducted with different types of waste. Yields are shown below (volume of ethanol produced pr. tonne dry matter).

| Type of waste | High cellulase loading L ethanol/ton dry matter | Low cellulase loading L ethanol/ton dry matter |
| --- | --- | --- |
| Unsorted MSW | 60-75 | 60 |
| Source sorted organic MSW | 110-140 | |
| Garden refuse (mainly lignocellulose), pre-treated at atmospheric pressure | | 10-20 |

-continued

| Type of waste | High cellulase loading L ethanol/ton dry matter | Low cellulase loading L ethanol/ton dry matter |
|---|---|---|
| Garden refuse (mainly lignocellulose), pre-treated at high pressure | | 112 |
| Drained manure | 20 | |
| Waste from potato flour production | 235 | |

Results demonstrate that considerable amounts of ethanol can be produced from MSW even at low enzyme loadings in this process. Having in mind, that sorting after fermentation is the strength of this process, results also illustrate that source sorting will increase the yield pr ton dry matter. The experiments with garden refuse illustrates the importance of high temperature pre-treatment for waste fractions mainly consisting of lignocellulose, and stresses that this process aiming at converting easy accessible monosaccharides into ethanol or other fermentation products. Even though, it is possible to reach an ethanol concentration of around 4 vol. % in the fermentation broth, which is necessary keeping economy in the distillation. This is possible because of the high dry matter content this process is operated in.

CITED LITERATURE

Giovannozzi-Sermanni, G., D'Annibale, A., Perani, C., Porri, A., Falesiedi, G. (2002). Solid-state bioreactors for the sustainability. Internet address
reCulture®: EP 0921858, EP 97935926.2
Dewaster®: http://www.ewoc.dk/
U.S. Pat. No. 4,342,820 A
U.S. Pat. No. 4,093,516 A
CZ 9,602,835 A3
U.S. Pat. No. 4,094,740 A
U.S. Pat. No. 5,637,502

The invention claimed is:

1. A method of processing unsorted municipal solid waste (MSW) comprising organic matter and inorganic matter, said method comprising:
    subjecting said unsorted MSW to non-pressurized thermal pre-treatment, followed by
    hydrolyzing said unsorted MSW by enzymatic hydrolysis so as to liquefy fermentable parts of said unsorted MSW to produce liquefied fermentable parts of said unsorted MSW, in the presence of non-fermentable solids, said unsorted MSW having a dry matter content of 20-50% (w/w) during said hydrolysis, followed by
    separating the liquefied fermentable parts of said unsorted MSW from the non-fermentable solids,
    wherein the enzymatic hydrolysis is carried out in a vessel along with free fall mixing of said unsorted MSW,
    wherein the separated liquefied fermentable parts of the unsorted MSW are subsequently subjected to fermentation, and
    wherein said unsorted municipal solid waste can comprise source-sorted MSW comprising organic and inorganic matter.

2. The method according to claim 1, wherein said fermentation is anaerobic fermentation.

3. The method according to claim 1, wherein the liquefied fermentable parts are subjected to fermentation using an ethanologenic microorganism.

4. The method according to claim 1, wherein the liquefied fermentable parts are subjected to fermentation involving addition of nitrogen sources.

5. The method according to claim 1, wherein the liquefied fermentable parts are subjected to fermentation involving addition of nutrients or vitamins.

6. The method according to claim 1, wherein the non-pressurised thermal pre-treatment is performed using steam.

7. The method according to claim 1, wherein the treatment time of the non-pressurised thermal pre-treatment is between 5-100 min. with a temperature ranging between 80-100° C. and a steam admission of 0.01-1.5 kg/kg dry matter.

8. The method according to claim 1, wherein the enzymatic hydrolysis is performed with hydrolytic enzymes, supplied in either native form or in the form of microbial organisms giving rise to the accumulation of such enzymes.

9. The method according to claim 1, wherein said enzymatic hydrolysis lasts for 5-96 hours and with a temperature ranging from 20-105° C.

10. The method according to claim 1, wherein the enzymatic hydrolysis is conducted using a mixture of enzymes including cellulases and hemicellulases.

11. The method according to claim 1, wherein the enzymatic hydrolysis is conducted using a mixture of enzymes including proteolytic enzymes.

12. The method according to claim 1, wherein the enzymatic hydrolysis is conducted using a mixture of enzymes including alpha amylases and glyco amylases.

13. The method according to claim 1, wherein the enzymatic hydrolysis is conducted using a mixture of enzymes including lipases.

14. The method according to claim 1, wherein the enzymatic hydrolysis is conducted using a mixture of enzymes including oxidative enzymes.

15. The method according to claim 1 wherein the sorting of the liquefied fermentable parts of the waste from the non-fermentable solids is performed by a sieve system.

16. The method according to claim 1, wherein the unsorted MSW is subjected to mechanical pre-treatment prior to enzymatic hydrolysis.

17. The method according to claim 16, wherein said mechanical pre-treatment comprises shredding or pulping.

18. The method of claim 1, wherein the dry matter content of said unsorted MSW is 20-45% w/w during said hydrolysis.

19. A method of processing unsorted municipal solid waste (MSW) comprising:
    subjecting said unsorted MSW to non-pressurized thermal pre-treatment, followed by
    adding hydrolysis enzymes to said pretreated unsorted MSW and hydrolyzing said pretreated unsorted MSW by enzymatic hydrolysis so as to liquefy fermentable parts of the pretreated unsorted MSW to produce liquefied fermentable parts of the pretreated unsorted MSW, in the presence of non-fermentable solids, said pretreated unsorted MSW having a dry matter content of 20-80% (w/w) during said hydrolysis, followed by
    separating the liquefied fermentable parts of said pretreated unsorted MSW from the non-fermentable solids,
    wherein said hydrolysis enzymes comprise at least one enzyme selected from the group consisting of cellulases, hemicellulases, proteolytic enzymes, alpha amylases, glycoamylases, lipases, and oxidative enzymes,
    wherein the enzymatic hydrolysis is carried out in a vessel along with free fall mixing of said pretreated unsorted MSW, and wherein said unsorted municipal solid waste can comprise source-sorted MSW comprising organic and inorganic matter.

20. The method of claim 19, further comprising fermenting said separated liquefied fermentable parts of said pretreated unsorted MSW.

* * * * *